(12) United States Patent
Hallmeyer et al.

(10) Patent No.: US 6,504,608 B2
(45) Date of Patent: Jan. 7, 2003

(54) OPTICAL MEASUREMENT ARRANGEMENT AND METHOD FOR INCLINATION MEASUREMENT

(75) Inventors: Klaus Hallmeyer, Kahla (DE); Joachim Wienecke, Jena (DE); Guenter Hoffmann, Jena (DE)

(73) Assignee: Leica Microsystems Jena GmbH, Jena (DE)

( * ) Notice: Subject to any disclaimer, the term of this patent is extended or adjusted under 35 U.S.C. 154(b) by 0 days.

(21) Appl. No.: 09/748,339

(22) Filed: Dec. 26, 2000

(65) Prior Publication Data

US 2001/0006419 A1 Jul. 5, 2001

(30) Foreign Application Priority Data

Dec. 27, 1999 (DE) .......................................... 199 63 345

(51) Int. Cl.$^7$ .................................................. G01J 4/00
(52) U.S. Cl. ........................ 356/369; 356/364; 356/609; 356/614; 356/326
(58) Field of Search ................................. 356/364–369, 356/609, 614, 619, 620, 622, 630, 634, 73, 319, 326, 237.1–237.4

(56) References Cited

U.S. PATENT DOCUMENTS

| | | | | |
|---|---|---|---|---|
| 3,880,524 A | * | 4/1975 | Dill et al. ..................... | 356/369 |
| 4,398,824 A | | 8/1983 | Feldman et al. ............. | 356/401 |
| 4,595,829 A | | 6/1986 | Neiimann et al. ........... | 250/201 |
| 4,712,912 A | * | 12/1987 | Messerschmidt ............. | 356/73 |
| 4,794,264 A | * | 12/1988 | Quackenbos et al. ....... | 356/237.1 |
| 5,136,149 A | | 8/1992 | Fujiwara et al. ............ | 250/201.5 |
| 5,179,422 A | * | 1/1993 | Peterson ...................... | 356/239 |
| 5,218,415 A | | 6/1993 | Kawashima ................. | 356/152 |
| 5,608,526 A | * | 3/1997 | Piwonka-Corle et al. ... | 356/369 |
| 6,091,499 A | * | 7/2000 | Abraham et al. ............ | 356/369 |
| 6,128,085 A | * | 10/2000 | Buermann et al. .......... | 356/369 |
| 6,184,984 B1 | * | 2/2001 | Lee et al. ..................... | 356/369 |
| 6,271,916 B1 | * | 8/2001 | Marxer et al. ............... | 356/237.3 |
| 6,304,326 B1 | * | 10/2001 | Aspnes et al. ............... | 356/369 |

* cited by examiner

Primary Examiner—Frank G. Font
Assistant Examiner—Sang H. Nguyen
(74) Attorney, Agent, or Firm—Foley & Lardner

(57) ABSTRACT

An optical measurement arrangement includes an ellipsometer (45) and a device for ascertaining and correcting directional deviations between the line normal to the specimen surface and the angle bisector (25) between the incident and return beams (23, 24) of the ellipsometer (45). A measurement arrangement includes a mirror objective and a device for ascertaining directional deviations between the line normal to the specimen surface and the optical axis of the mirror objective, which has a deflection element in the unused aperture space of the mirror objective. A direction monitoring beam (30) is directed onto the specimen (P). An optical element for imaging the return reflection of the direction monitoring beam (30) onto an area detector that is connected to an evaluation circuit (46) is also provided. Positioning commands for a specimen stage (12) are available at the outputs of the evaluation circuit (46). By way of the control commands, the specimen stage is caused to tilt until the return reflection on the area detector has assumed the position at which the direction of the normal line corresponds to the direction of the angle bisector (25).

24 Claims, 6 Drawing Sheets

OPTICAL MEASUREMENT ARRANGEMENT AND METHOD FOR INCLINATION MEASUREMENT

CROSS REFERENCE TO RELATED APPLICATIONS

This invention claims priority of a German filed patent application DE-P 199 63 345.2.

FIELD OF THE INVENTION

The invention refers to an optical measurement arrangement having an ellipsometer in which an incident beam of polarized light is directed at an angle $\alpha \neq 90°$ onto a measurement location on the surface of a specimen, and information as to specimen properties, preferably as to layer thicknesses, is obtained from an investigation of the reflected return beam; and having a device for ascertaining and correcting directional deviations between the line normal to the specimen surface and the angle bisector between the incident and return beams. The invention further refers to a measurement arrangement and a method having an objective for illumination and imaging of a measurement location on a specimen, and a leveling device having an optical radiation source, a direction monitoring beam, and a spatially resolving detector.

BACKGROUND OF THE INVENTION

Optical measurement arrangements on the principle of ellipsometers and spectrophotometers, and their use for layer thickness measurement, are known from the existing art. They have been successfully used, in particular, for the measurement of thin layers, for example on patterns on wafer surfaces.

Since an effort is being made toward increasingly fine patterns and increasingly thin layers in wafer manufacture in particular, more and more stringent requirements are also being placed on the accuracy of the optical measurement arrangements with which the dimensional consistency of the patterns and layers is verified. In this context, it is important not only to ensure that no pattern edges are located in the measurement window (since the layer thickness measurement can thereby be falsified), but above all to guarantee that the specimen surface at the measurement point is oriented perpendicular to the measurement beam path, so that measurement errors can be ruled out.

Obliquities or undesired inclinations of the specimen surface occur, for example, if the specimen itself has an uneven surface, is not resting in tilt-free fashion on the specimen stage, or is distorted by suction onto the support surface. Such obliquities therefore must be identified and compensated for by way of suitable positioning systems. In addition, an accurate measurement also requires precise focusing, i.e. it must be ensured that the specimen surface lies in the focal plane and that, in the event of deviations, the specimen can be correspondingly aligned.

In order to allow even complex patterns and layer systems to be measured, both ellipsometers and spectrophotometers are often used in a combined arrangement for measurement. A high degree of measurement reliability is thereby obtained, but the requisite large number of optical assemblies results in space problems, since the assemblies must be coordinated and positioned with respect to one another in such a way that, if possible, the beam paths do not substantially influence each other. For example, it is usual for direct access to the measurement location to be already blocked by the measurement objective of the spectrophotometer.

Additional problems arise because of the variable measurement locations on the specimen surface, i.e. a change in specimen position relative to the measurement beam paths occurs during the measurement or between individual measurement steps; if the mechanical positioning devices provided for the purpose are insufficiently precise, this can result in defocusing and also in tilting of the specimen surface.

Because not only the demand for greater accuracy but also the effort toward increasing production volumes must be taken into account, it is necessary—for example in continuous production of wafers—to make measurements at ever shorter intervals and to check prior to each measurement that the prerequisites for the necessary high measurement accuracy are present. If such is not the case, that check must be followed by a rapid and, if possible, automatic correction of the specimen orientation.

A large number of publications regarding the orientation of wafers in wafer steppers and regarding leveling relative to the measurement beam path is already known in the existing art. U.S. Pat. No. 4,398,824, for example, describes a method for orienting a wafer in which local obliquities of the wafer and inhomogeneities in the photoresist can be compensated for. This method can only be applied, however, if portions of the wafer are configured as Fresnel zones. Since this is usually not the case, however, the method proposed here is not suitable for the most common wafer production equipment.

U.S. Pat. No. 5,218,415 describes a device for determining the obliquity of a wafer relative to the measurement beam in which an arrangement for illuminating a measurement location on the wafer, a device for receiving the reflected light beam, and means for modifying the size of the light beam are provided. In this context, a determination is made of the size or cross section of the light beam in the optically conjugated plane of the surface to be measured.

U.S. Pat. No. 4,595,829 discloses an arrangement for focusing a specimen surface with which it is possible to determine the focal plane and cause a change in the position of the sample in such a way that the specimen surface lies in the focal plane. It is not possible with this arrangement to ascertain and correct a tilt of the specimen surface relative to the measurement beam path, however, so that the prerequisites for extremely accurate measurements cannot be created.

U.S. Pat. No. 5,136,149 describes a method for the inspection of wafer surfaces which makes possible both focusing and a determination of the obliquity of the wafer surface. In this case a beam is directed through an objective onto the specimen surface, and the light reflected there is split into two beams. Of these, the first beam is recorded by a position-sensitive line receiver (CCD line), and a focus signal is generated with the aid of this receiver. The second partial beam strikes a two-dimensional position-sensitive detector and is used there to determine the obliquity. A substantial disadvantage here is the fact that the determinations of focus and obliquity, and thus the adjustment possibilities when correcting focus and obliquity, are not decoupled.

If the measurement and correction possibilities for focus and obliquity are dependent on one another in this fashion, it is time-consuming to meet the desired criteria for both the focus and obliquity of the wafer, since correcting the one variable always brings about a change in the other, and the approximation to the ideal state must be made iteratively. For example, if the focus is established first and then the obliquity is corrected, the obliquity correction causes the focus to drift out again as a result of the obliquity correction. The requirements in terms of obliquity have now been met, but the specimen surface is not adequately focused. If the focus is subsequently corrected, there is once again the risk of a change in the leveling or orientation of the wafer surface with respect to the measurement arrangement, and the leveling must once again be checked and, if necessary, corrected. This alternating adjustment until the desired result is achieved does not meet the need for a rapid inspection and production pace.

SUMMARY OF THE INVENTION

Proceeding therefrom, it is the object of the invention to develop an optical measurement arrangement of the kind cited initially in such a way that local inclinations and irregularities of the specimen surface are identified and a correction of the inclinational deviation of the specimen surface with reference to the optical axis of the measurement arrangement is made, said correction being performed with high accuracy and in a brief period of time, and being decoupled from any focusing of the specimen surface.

According to the present invention, the object is achieved by an optical measurement arrangement having an ellipsometer in which an incident beam of polarized light is directed at an angle $\alpha \neq 90°$ onto a measurement location on the surface of a specimen, and information as to specimen properties, preferably as to layer thicknesses, is obtained from an investigation of the reflected return beam;

a device for ascertaining and correcting directional deviations between a line normal to the specimen surface and an angle bisector between the incident and return beams;

an optical radiation source emitting a direction monitoring beam which is directed onto the measurement location substantially in the direction of the angle bisector;

a position-sensitive area detector and optical means for imaging a return reflection of the direction monitoring beam onto the position-sensitive area detector;

an evaluation circuit to which the position-sensitive area detector is connected and said evaluation circuit is for determining positions commands; and a positioning system receiving the positioning commands of the evaluation circuit, wherein a specimen stage on which the specimen rests is caused to tilt until the position of the return reflection of the direction monitoring beam on the position-sensitive area detector corresponds to a predefined position at which the direction of the line normal to the specimen surface corresponds to the direction of the angle bisector.

A further object of the invention is to describe a measurement arrangement with which local inclinations and irregularities of a specimen surface can be detected, with high accuracy and independently of any focusing.

This object is achieved, according to the invention, by a measurement arrangement comprising a mirror arrangement having a central mirror that defines a shadow region and an optical axis, the mirror arrangement illuminating and imaging a measurement location on a specimen, a leveling device having an optical radiation source, a direction monitoring beam, and a spatially resolving detector and at least one optical means being arranged in the shadow region of the central mirror of the mirror arrangement, wherein said at least one optical means guides the direction monitoring beam substantially along the optical axis of the mirror arrangement and directs it onto the measurement location of the specimen, and wherein said at least one optical means directs the direction monitoring beam reflected from the measurement location onto the spatially resolving detector.

A further object of the invention is to describe a method with which local inclinations and irregularities of a specimen surface can be detected, with high accuracy and independently of any focusing.

This object is achieved, according to the invention, by a method for measuring the inclination between a line perpendicular to a measurement location on a specimen and an optical axis defined by an objective for imaging the measurement location, characterized by the following steps:

generating a direction monitoring beam by a radiation source;

delivering the direction monitoring beam to the optical axis of the objective, wherein the direction monitoring beam arrives in a region between the objective and the measurement location;

deflecting the direction monitoring beam toward the measurement location;

reflecting the direction monitoring beam at the measurement location;

deflecting the reflected direction monitoring beam out of the vicinity of the optical axis, specifically in a region between the objective and the measurement location;

receiving the deflected direction monitoring beam by a spatially resolving detector; and determining from the signals of the detector the inclination between the line perpendicular to the measurement location and the optical axis of the objective.

Advantageous embodiments and developments of the invention follow from the subclaims.

According to the present invention, in an optical measurement arrangement having an ellipsometer and having a device for ascertaining and correcting directional deviations between the line normal to the specimen surface and the angle bisector between the incident and return beams of the ellipsometer, provision is made for a direction monitoring beam to be directed onto the specimen substantially in the direction of the angle bisector, its arrival point lying in the arrival point of the incident beam of the ellipsometer; for optical means for imaging the return reflection of the direction monitoring beam onto an area detector to be provided; for the area detector to be connected to an evaluation circuit; and for positioning commands for a positioning system connected to the specimen stage to be available at the outputs of the evaluation circuit, the positioning commands causing tilting of the specimen stage until the position of the return reflection on the area detector corresponds to the predefined position at which the direction of the normal line corresponds to the direction of the angle bisector.

If what is provided as the area detector is, advantageously, a four-quadrant detector, the proportional quantities of light of the return reflection striking each quadrant can serve as evaluation criteria for deviations between the direction of the normal line and the direction of the angle bisector. Tilting of the specimen stage on which the specimen rests can be brought about as a function of the deviations thus ascertained.

The result is to create an arrangement that makes possible alignment of the specimen surface with little technical complexity and high efficiency. The receiving surface of the four-quadrant detector is advantageously adjusted in such a way that the direction of the angle bisector corresponds precisely to the direction of the normal line when the same quantities of light are striking all four quadrants.

In an embodiment of the invention, a focussable diode laser that emits linearly polarized light at, for example, a wavelength λ=670 nm is provided as the source for the direction monitoring beam. A polarization splitter is present in the beam path between the diode laser and the specimen surface, followed (from the viewpoint of the diode laser) by a λ/4 plate. On its path to the specimen, the linearly polarized light is converted into circularly polarized light as it passes through the λ/4 plate. On the return path from the specimen, another pass through the λ/4 plate turns the circularly polarized light back into linearly polarized light, but with a polarization of π/2, which is advantageously used to couple out the return reflection at the splitter surface of the polarization splitter. From the splitter surface, the reflected direction monitoring beam is directed onto the receiving surfaces of the four-quadrant sensor, where evaluation of its position is performed in the manner already described. It is thereby possible to achieve an efficient and economical configuration of the measurement arrangement with prefabricated optical assemblies.

It is also within the context of the invention, however, to direct the light of the diode laser without interposition of a polarization splitter and a λ/4 plate via the deflection mirror onto the specimen surface and from there back onto the four-quadrant sensor; the advantageous result is that the number of optical assemblies to be used can be reduced, and principally that assemblies which greatly attenuate the intensity can be eliminated from the beam path.

An embodiment of this kind is achieved, for example, if the direction monitoring beam is directed onto the specimen surface not exactly in the direction of the angle bisector, so that the direction monitoring beam reflected from the specimen surface does not return back into the incoming beam, and the four-quadrant sensor can be placed directly in the reflected beam path. Separate guidance of the beams also yields the advantage that mutual influence between the light of the direction monitoring beam incident onto and returning from the specimen is not possible.

Of course the invention is not limited exclusively to the use of diode lasers per se, and also not to the wavelength λ=670 nm; other suitable radiation sources and wavelengths are conceivable.

In a further preferred embodiment, the positioning system for tilting the specimen stage comprises two piezo-translators, each of which has one end articulated on the frame and the second end braced against the specimen stage, the specimen stage resting in the manner of a three-point mount on these two ends of the translators and on a frame-mounted bearing point, and these three support positions being distributed with radial symmetry on a circular circumference.

In particular when the measurement arrangement according to the present invention is used in conjunction with the inspection or measurement of layer thicknesses on wafer surfaces, piezo-translators having a stroke length of 200 μm should be provided, while the frame-mounted bearing point can be configured as a prism support, the distance between the support positions on the circular circumference advantageously being approximately 120 mm.

The invention further refers to a measurement arrangement comprises a mirror arrangement, especially a mirror objective, whose central mirror forms a shadow region (unused aperture space of the mirror arrangement). Arranged in this shadow region are optical means that direct a direction monitoring beam of a leveling device substantially along the optical axis of the mirror arrangement onto a measurement location on the specimen, and direct the direction monitoring beam reflected from the measurement location onto a spatially resolving detector.

This makes possible a particularly compact and space-saving configuration of the measurement arrangement. In particular, the beam path of the leveling device is separate from the normal beam path of the mirror arrangement. The result is to eliminate the scattered light of the direction monitoring beam that otherwise occurs at single-mirror elements and interferes with the measured and received radiation. In this fashion it is possible, as will be explained below, to direct onto the specimen surface a plurality of beams that have a common optical axis but whose emissions nevertheless do not pass through one another.

For beam guidance for the leveling device, it is possible on the one hand to provide a beam splitter with which the direction monitoring beam reflected from the measurement location is coupled out of the beam path of the illuminating direction monitoring beam and guided onto the detector. This is necessary when the direction monitoring beam runs parallel to the optical axis of the mirror arrangement. If the measurement location is aligned exactly perpendicular to the optical axis. the direction monitoring beam from the measured specimen will reflect back into itself. On the other hand, the beam paths of the illuminating and reflected direction monitoring beams can be somewhat different from one another, and can have a slight inclination with respect to the optical axis. In this case a deflection mirror or deflection prism is sufficient to direct the reflected direction monitoring beam onto the detector. The slightly different inclination of the illuminating and reflected direction monitoring beams with respect to the optical axis of the measurement arrangement is taken into account in the evaluation of the detector signals, in order to make possible an accurate determination of the inclination of the measurement location with respect to the optical axis of the measurement arrangement.

Also possible, of course, is an arrangement having two deflection elements between the arrangement and the measurement location, of which the one deflection element directs the direction monitoring beam onto the measurement location, and the other directs the reflected direction monitoring beam onto the detector.

In addition, using an evaluation circuit and a positioning system, the inclination of the specimen with the measurement location present thereon can be modified in such a way that deviations between the line perpendicular to the measurement location and the optical axis of the measurement arrangement are adjusted or controlled to a predetermined value or to zero.

The leveling device is used concurrently with normal operation of the mirror arrangement. In such operation, the mirror arrangement delivers optical radiation to the measurement location and receives the radiation coming from the measurement location. The mirror arrangement is thus used for illumination purposes and for visual or electronic observation of the measurement location and/or to pass the optical radiation through to a focusing device and/or to receive for a spectrophotometer the radiation coming from the measurement location. In addition, an ellipsometer, in particular also a spectral ellipsometer, can also be directed with a separate beam path onto the measurement location.

The invention furthermore refers to a method for measuring the inclination of a measurement location on a specimen imaged by an objective, in which a direction monitoring beam is generated by a radiation source and brought to or into the vicinity of the optical axis of the objective in a region between the objective and the measurement location. There it is deflected toward the measurement location. After reflection of the direction monitoring beam at the measurement location, the reflected direction monitoring beam is deflected out of the vicinity of the optical axis in the region between the measurement location and the objective, and directed onto a spatially resolving detector. From the detector signals, the inclinational deviation of the line perpendicular to the measurement location from the optical axis of the objective is determined.

In this context, the direction monitoring beam can extend, in the region between the objective and the measurement location, parallel to the optical axis of the objective or at a slight inclination with respect to the optical axis of the objective. In the case where the direction monitoring beam is oriented parallel to the optical axis, evaluation of the detector signals for determining the inclination of the measurement location is independent of any focusing of the measurement location with a focus measurement system. The inclination of the measurement location can thus advantageously be ascertained and corrected separately from the focus state.

In the case of a direction monitoring beam that is slightly inclined with respect to the optical axis, that inclination (in the range 0–2°) is taken into account either in the adjustment of the detector or in the evaluation of the detector signals. Here again, evaluation of the detector signals is substantially independent of focusing with a focusing device. Fewer optical components are needed for inclination measurement, however, than in the case in which the direction monitoring beam extends parallel to the optical axis.

The method described above for inclination measurement can be used for any objective that records and images the measurement location. On the one hand a conventional objective having lenses can be used. The direction monitoring beam is deflected between the objective and the measurement location by means of a deflecting optical element. The deflecting optical element (e.g. beam splitter, mirror) can disturb the optical beam path of the objective. However, the disturbance is negligible if the deflecting optical element is very near to the objective and is greater or much smaller than the diameter of the end-lens of the objective (the end-lens is defined as the lens of the objective nearest to the measurement location).

On the other hand the method described above is usable in particular in the case of a mirror objective in whose unused aperture space, i.e. in the shadow region of the central mirror of the mirror objective, the deflection of the direction monitoring beam to or from the measurement location can be accomplished without colliding with other beam paths of the mirror objective.

In addition, the inclination of the specimen can be adjusted, with the aid of an evaluation circuit and a positioning system, in such a way that a predefined angle is created between the line perpendicular to the measurement location on the specimen and the optical axis of the objective. This angle can also be set to zero, or can be established by way of a control system so that the optical axis of the objective is perpendicular to the measurement location.

A particularly preferred variant embodiment of a measurement arrangement according to the present invention is achieved in cases in which in addition to the ellipsometer, there is also provided a spectrophotometer that, in addition to the measurement with the ellipsometer, can also be used for layer thickness measurement. Here a specimen measurement beam is focused through a mirror objective onto the specimen surface, and the light of the specimen measurement beam reflected back from the specimen into the mirror objective is conveyed to a spectrograph for evaluation. The specimen measurement beam forms a hollow beam cone, proceeding from the mirror objective, which stands with its conical tip on the measurement location and in which the space in the interior of the cone is not used by the specimen measurement beam. In other words the mirror objective has, in the direction toward the specimen, an open aperture space which is not used by the specimen measurement beam and whose three-dimensional extent corresponds to the interior of the hollow cone.

In order to decouple from one another the optical means and method steps for leveling the specimen and correcting angular offsets of the specimen surface, and the optical means and method steps for spectrophotometric sensing of the specimen properties, and thus to prevent any mutual influence from occurring, provision is made according to the present invention for guiding the direction monitoring beam inside the hollow cone or in the open aperture space not used by the mirror objective.

For this purpose, a deflection mirror having a mirror surface inclined preferably 45° toward the optical axis of the mirror objective is arranged, inside this unused aperture space, between the mirror objective and specimen surface. The direction monitoring beam coming from the diode laser and focused onto the specimen surface is first directed laterally through the hollow beam cone onto the mirror surface of the deflection mirror, and from the latter is deflected toward the specimen surface. The result of this guidance of the direction monitoring beam inside the hollow beam cone of the specimen measurement beam is that the direction monitoring beam and specimen measurement beam can be simultaneously focused onto the same measurement point, and do not (or do not significantly) influence one another.

From the specimen surface, the direction monitoring beam is reflected back into the unused aperture space of the mirror objective, proceeds inside the unused aperture space to the deflection mirror, and is directed by the latter, as already described, directly or indirectly onto the four-quadrant sensor. The outer contour of the deflection mirror should advantageously be adapted to the internal shape of the hollow beam cone, so that the aperture space not used by the mirror objective can be optimally utilized for the direction monitoring beam.

The particular advantage, as already indicated, is the fact that decoupling of the beam paths is guaranteed and that nevertheless a compact configuration can also be achieved, in which the large number of necessary optical assemblies are accommodated in the vicinity of the measurement location.

These highly accurate measurement arrangements of course also include a capability for monitoring and correcting the focal position of the specimen surface with reference to the measurement beam paths of the ellipsometer and spectrophotometer. In addition to the optical assemblies already referred to, a focus measurement and adjustment system is therefore also present. In this, based on a known embodiment, a focus measurement beam is directed obliquely onto the specimen surface through a half-occluded pupil, and a position-sensitive detector is arranged in the light reflected from the specimen surface. When the specimen is displaced in the direction of the optical axis, a measurement signal that changes in proportion to the displacement distance is available at the output of the detector, and on the basis of this the focal position can be ascertained and corrected.

The focus measurement beam, like the specimen measurement beam used for spectrophotometry, is directed through the mirror objective onto the measurement location, while the direction monitoring beam is emitted into the region between mirror objective and specimen surface, and is directed onto the measurement location by the deflection mirror positioned there.

The features according to the present invention thus yield an optical measurement arrangement that on the one hand has available all the assemblies and components necessary to perform the measurement task, and nonetheless can be configured in such a way that the large number of measurement tasks and steps concentrated onto a very small portion of the specimen surface can be performed without hindrance.

BRIEF DESCRIPTION OF THE DRAWINGS

The invention will be explained below in more detail with reference to an exemplary embodiment. In the appended drawings.

DETAILED DESCRIPTION OF THE INVENTION

Figure 1:
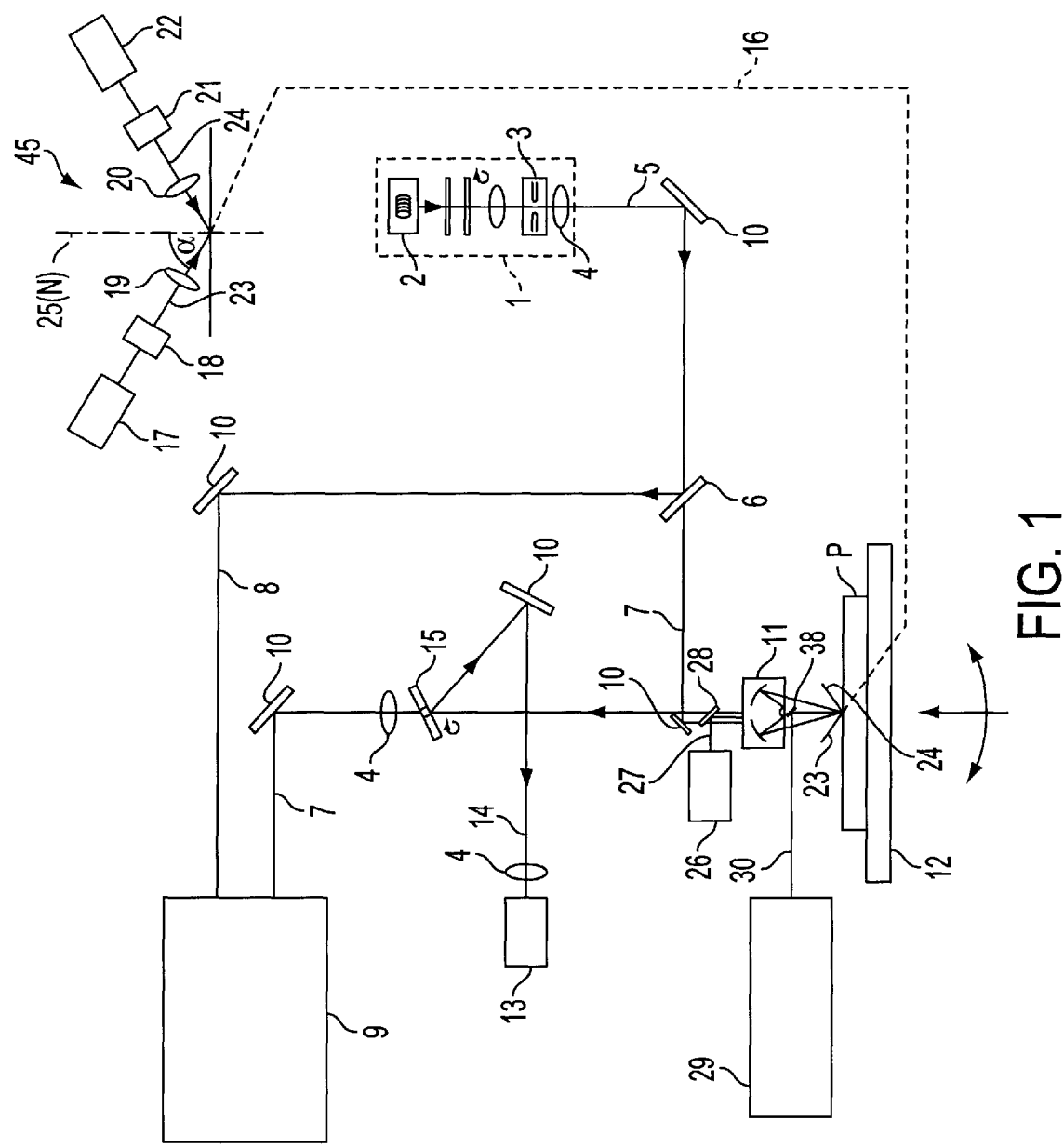
FIG. 1 shows the overall configuration of an optical measurement arrangement having an ellipsometer, spectrophotometer, leveling device, and focus measurement device.

The invention will be explained below, by way of example, with reference to an optical layer thickness measurement system which is part of a wafer production line and with which the intended wafer pattern can be monitored directly. A measurement arrangement of this kind is depicted schematically in FIG. 1.

The measurement arrangement comprises firstly the optical assemblies of a spectrophotometer, having an illumination apparatus 1 in which is provided a halogen lamp 2 whose filament is imaged in the opening of a deuterium lamp 3 that is also part of illumination apparatus 1. The light from these two lamps 2, 3, which is filtered if applicable, is concentrated with suitable lenses 4 into an illuminating beam 5.

By way of mirrors, lenses, and stops whose arrangement in such cases is familiar to those skilled in the art and therefore need not be explained further here, illuminating beam 5 reaches a beam splitter 6, for example a semitransparent mirror, at whose splitter surface illuminating beam 5 is split into a specimen measurement beam 7 and a reference beam 8, optionally with different intensities for the two beams.

Reference 8 is conveyed, again with the aid of suitably arranged optical assemblies such as mirrors and lenses, to a spectrograph 9.

Specimen measurement beam 7, on the other hand, after a change in direction by way of deflection mirror 10, is directed through a mirror objective 11 onto a specimen P, in this case a wafer, that is placed on a specimen stage 12.

Specimen measurement beam 7 illuminates a target area on specimen P, and the light reflected back from the specimen surface into mirror objective 11 is then also conveyed to spectrograph 9. Here, in known fashion, the measurement light and reference light are spectrally dispersed for evaluation, and at the same time imaged onto a CCD matrix that is integrated into the spectrograph (and not separately depicted in the drawing).

It can be assumed that the spectrophotometry method is sufficiently known, and that further explanation at this juncture is once again superfluous.

Advantageously, a CCD camera 13 is provided, serving to display on a monitor the area of the specimen surface being examined, so as thereby to allow visual selection of a portion that is preferably to be monitored. A pinhole mirror 15 is provided to couple beam 14, which serves for visual observation, into and out of specimen measurement beam 7 coming from specimen P.

To allow even complex layer systems on wafers to be measured reliably and with high accuracy, not only the spectrophotometer previously described but also an ellipsometer 45 is used in the measurement arrangement selected for explanation, so that the measurement result can be determined with two measurement methods.

For reasons of clarity, the assemblies of ellipsometer 45 are depicted separately in FIG. 1, specifically at the top right. The relationship of the ellipsometer assemblies to measurement location M on specimen P is indicated by a dashed line 16.

Ellipsometer 45 is used to measure the same pattern or measurement location M as the spectrophotometer. For this purpose, the light of a xenon lamp 17 is directed via a polarizer 18 and a lens 19 onto measurement location M. The light reflected from measurement location M reaches evaluation unit 22 through an objective 20 and an analyzer 21.

Since linearly polarized light with a predefined polarization direction and wavelength is directed at a large angle α onto the surface of specimen P, upon reflection at the specimen surface the wave amplitude and the phase of the polarization components parallel and perpendicular to the plane of incidence are modified differently. An examination of the polarization state thus offers the possibility of drawing conclusions as to the surface pattern and layer thicknesses at measurement location M.

The assemblies of ellipsometer 45 are arranged in such a way that incident beam 23 and return beam 24 are guided laterally past mirror objective 11. To illustrate this, FIG. 1 additionally depicts incident beam 23 and return beam 24 of ellipsometer 45 in outline fashion above specimen P resting on specimen stage 12.

An important prerequisite for accurate measurements of layer thicknesses of small patterns is firstly that no pattern edges be located in the measurement window, since otherwise the result of the layer thickness measurement would be falsified; and secondly that the surface of specimen P lie, at least at the measurement position, perpendicular to specimen measurement beam 7 incident upon the surface, and also perpendicular to angle bisector 25 of the angle enclosed by incident beam 23 and return beam 24. In other words, line N normal to specimen P at measurement location M, the direction of incidence of specimen measurement beam 7 onto specimen P, and angle bisector 25 must all coincide with the greatest possible accuracy. FIG. 1 symbolizes the ideal state, by depicting line N normal to the specimen surface superimposed on angle bisector 25. To illustrate this, the reference character for normal line N is shown in FIG. 1 in parentheses next to angle bisector 25.

This criterion requires that before each layer thickness measurement, any tilt of normal line N that may be present with respect to specimen measurement beam 7 and angle bisector 25 must be ascertained and corrected. Tilts or obliquities of this kind can result if the wafer itself is irregular at its surface and/or has been unevenly placed onto or drawn against specimen stage 12.

As a further prerequisite for high measurement accuracy, precise focusing of measurement location M must be guaranteed. For this purpose, the measurement arrangement is equipped with a focus measurement system 26 which is, for example, a laser autofocus system in accordance with a principle known from the existing art. In this, as indicated in FIG. 1, the light of a laser diode in the form of a focus measurement beam 27 is directed with a mirror 28 into specimen P. In the beam path of focus measurement beam 27, half the pupil is occluded, so that its light falls obliquely onto the specimen surface. Only when the specimen surface is in the focal plane is a light spot symmetrical with respect to the optical axis created. If the specimen surface is displaced in the direction of the optical axis, i.e. if the specimen surface lies outside the focal plane, the light spot is displaced laterally with respect to the optical axis. The result is therefore to generate a measurement signal which is proportional to the deviation from the focal plane and which can be used by way of an associated positioning system to adjust the focal position.

The measurement arrangement described above must therefore be able to meet the following criteria in order for highly accurate measurement of layer thicknesses to be possible:

first, the surface area having patterning that is as homogeneous as possible must be selected for measurement;

specimen stage 12 must then be caused to move in such a way that the pattern to be measured comes into the target region, CCD camera 13 being usable to locate and capture measurement location M;

in the next step, any deviation of line N normal to the specimen surface at measurement location M from the direction of the incident specimen measurement beam 7 of the spectrophotometer and from angle bisector 25 between incident beam 23 and return beam 24 of ellipsometer 45 must be ascertained;

if a deviation is detected, specimen P must be leveled, i.e. specimen stage 12 with specimen P on it must be tilted so as to compensate for angular errors;

before the measurement can be made, the focal position of the specimen surface at measurement location M must be checked and (if necessary) corrected, for which purpose focus measurement system 26 that is present, including a downstream positioning device for displacing specimen stage 12 in the direction of the optical axis, is used;

after these position corrections, the actual measurements can then be performed, i.e. measuring the layer thickness either with the spectrophotometer or with ellipsometer 45 or with both, as well as further investigations of the patterns on specimen P.

In the description hereinafter, the procedure for correcting positional deviations of normal line N from angle bisector 25 will be referred to using the simplified term "leveling." With arrangements and methods known from the existing art for leveling and for correcting focal position, the general problem exists that the steps necessary for leveling and for focusing cannot be performed independently of one another.

For example, first the focal position must be ascertained and corrected so that the orientation of normal line N can be measured. To compensate for directional deviations of normal line N from angle bisector 25, specimen P must be tilted, which results in undesired defocusing. The focal position must therefore be measured again and refocused. Following refocusing, a check must be made as to whether the leveling is still OK, and any deviations must be corrected.

It is thus easy to see that the dependence between leveling and focusing is disadvantageously time-consuming and consequently also incompatible with the desire for a rapid production pace in continuous or mass production.

According to the present invention, a leveling device 29 whose direction monitoring beam 30 is directed onto the specimen surface at measurement location M is provided in order to correct the leveling or to compensate for angular deviations between line N normal to the specimen surface at measurement location M and angle bisector 25.

Figure 2:
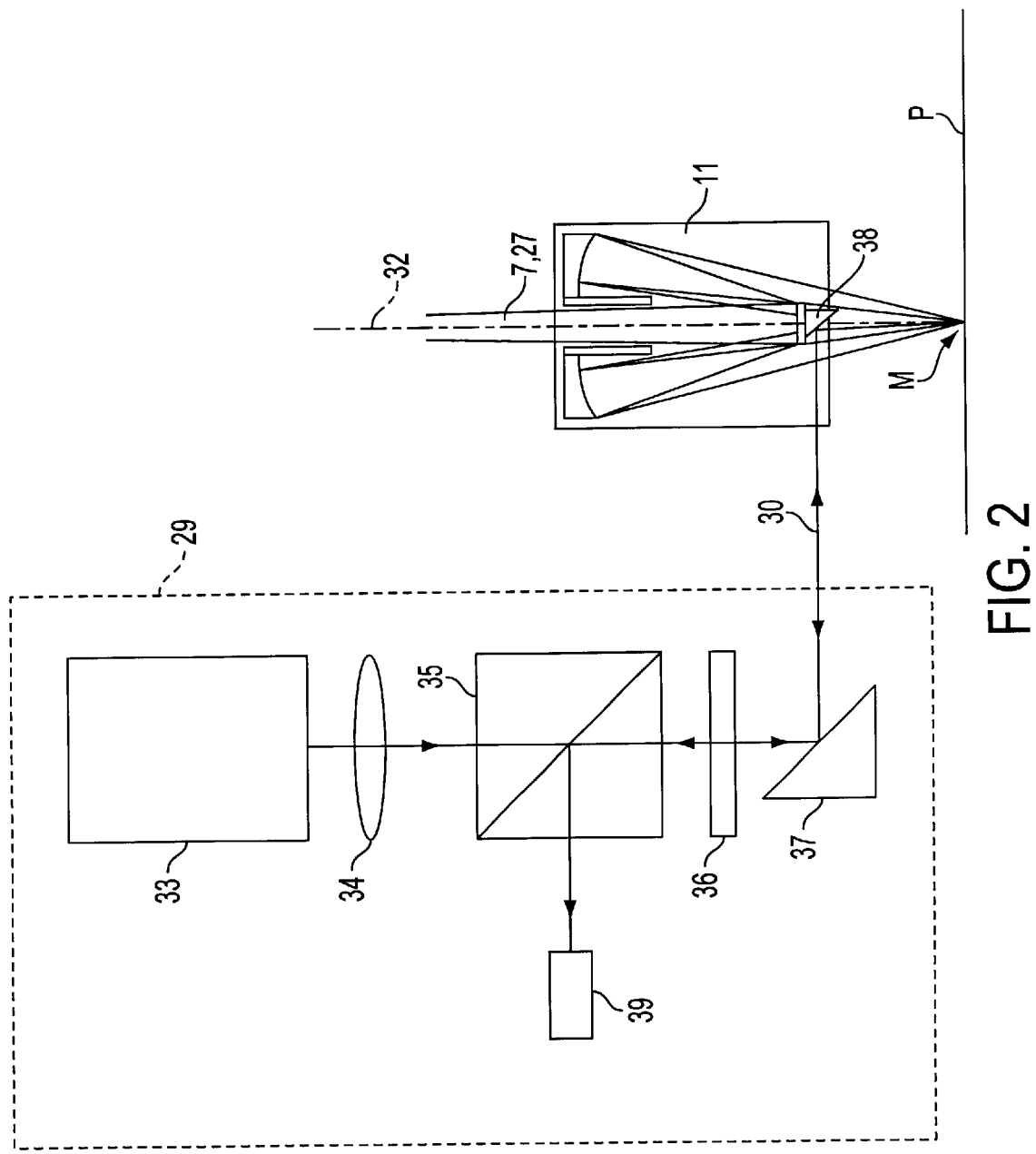
FIG. 2 shows a first variant of the manner in which the direction monitoring beam is guided according to the present invention.

FIG. 2 depicts a first variant of leveling device 29. Mirror objective 11 with its optical axis 32 are shown here, and the beam paths of specimen measurement beam 7 and focus measurement beam 27, which are directed through mirror objective 11 onto measurement location M, are also indicated.

As shown in FIG. 2, leveling device 29 substantially comprises a diode laser 33 whose linearly polarized light, preferably at a wavelength $\lambda=670$ nm, is focused by way of an optical system 34 onto measurement location M. A polarization splitter 35, a $\lambda/4$ plate 36, a deflection mirror 37, and a deflection mirror 38 are provided as further optical assemblies. The linearly polarized laser light of diode laser 33 is converted into circularly polarized light as it passes through $\lambda/4$ plate 36, and reaches measurement location M via deflection mirrors 37 and 38.

On its return trip, the circularly polarized light of direction monitoring beam 30 reflected from measurement location M, deflected again in reverse order by deflection mirrors 38 and 37, once again passes through the $\lambda/4$ plate and is thereby turned back into linearly polarized light, but with a polarization rotation of $\pi/2$. Because of the change in polarization direction, the return reflection of direction monitoring beam 30 can be coupled out at the splitter surface of polarization splitter 35, the coupled-out portion being directed onto a four-quadrant sensor 39.

In order to achieve the greatest possible decoupling of the optical means and method steps for leveling from those for measuring and correcting the focal position, according to the present invention deflection mirror 38 is arranged in the unused open aperture space of mirror objective 11.

Figure 3:
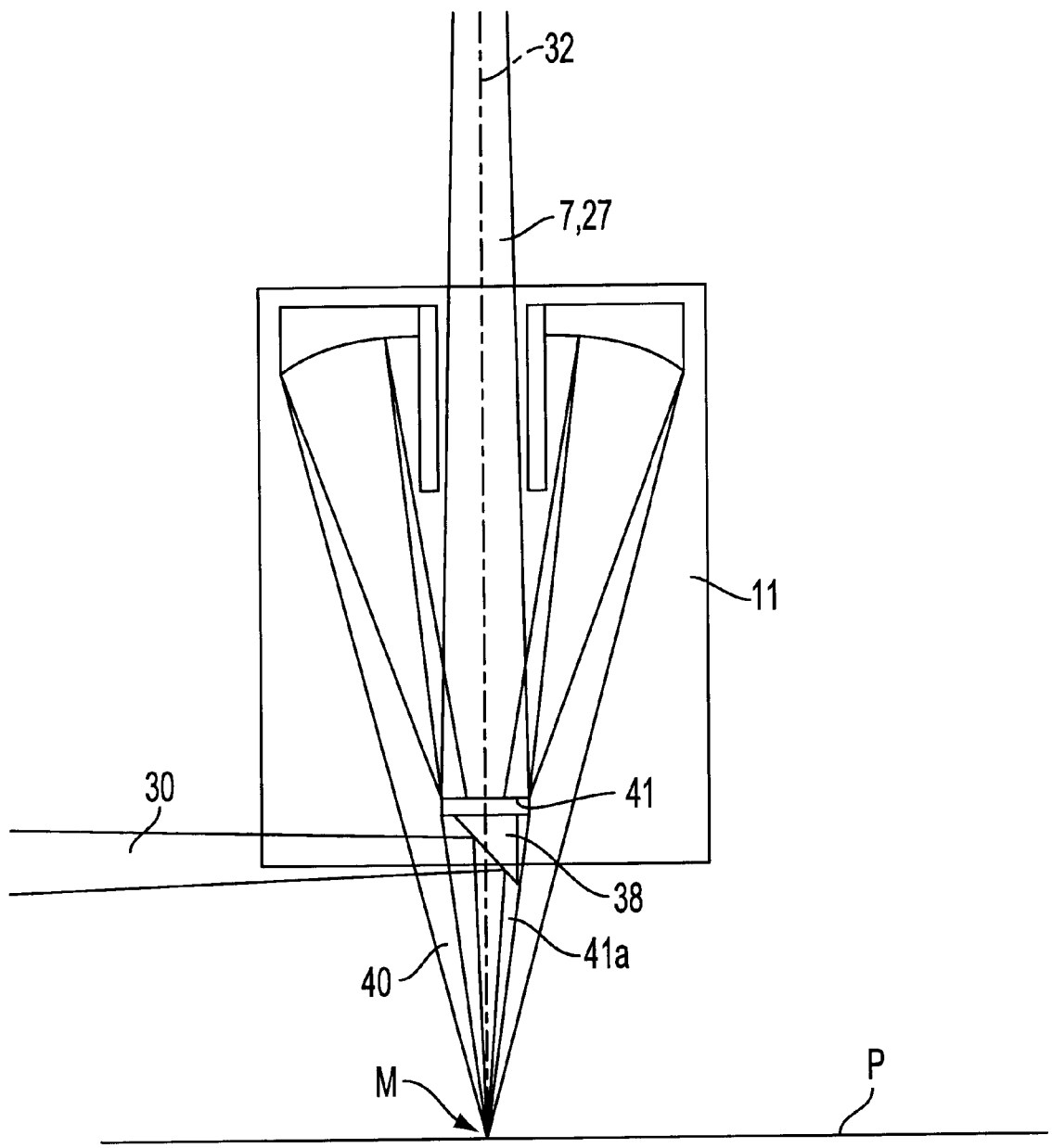
FIG. 3 shows the arrangement of a deflection mirror for the direction monitoring beam on the mirror objective.

This is illustrated in FIG. 3, which shows mirror objective 11 enlarged even more greatly than in FIG. 2. The focused direction monitoring beam 30 coming from diode laser 33 is first directed laterally through hollow beam cone 40 of mirror objective 11 onto deflection mirror 38, and is deflected by the latter toward specimen P. Direction monitoring beam 30 and hollow beam cone 40 in which specimen measurement beam 7 and focus measurement beam 27 extend are thus directed in spatially separated fashion onto specimen P. Direction monitoring beam 30 on the one hand, and specimen measuring beam 7 and focus measuring beam 27 on the other hand, are thus focused simultaneously onto the same measurement location M without substantially influencing one another.

Deflection mirror 38 can advantageously be attached (not depicted in the drawing) to the mount of central mirror 41 of mirror objective 11, and should be configured, as indicated in FIG. 2 and in FIG. 3, as a truncated cone so that its outer contour is adapted to the inner contour of hollow beam cone 40. Not only does this ensure an unobstructed aperture for mirror objective 11, but also the aperture space not used by mirror objective 11, i.e. shadow region 41a of central mirror 41, can be optimally used for the guidance of direction monitoring beam 30.

The fact that direction monitoring beam 30 is directed in focused fashion onto measurement location M reduces the probability that pattern edges which might falsify the measurement result will be located in the measurement region. The use of a diode laser 33 with a wavelength $\lambda=670$ nm additionally makes it possible to keep the measurement spot small, which further reduces the probability that pattern edges will be present in the measurement region. When adjusting the assemblies, it is important to ensure that the spot directed via direction monitoring beam 30 onto measurement location M is reliably located, in terms of both size and alignment and stability tolerance, in the incidence point of incident beam 23 of ellipsometer 45.

The size of the receiving surface and the position of four-quadrant detector 39 are matched to the size of the reflected direction monitoring beam 30, which in turn depends on the length of the optical path between the measurement location and the receiving surface. Advantageously, the receiving surface should be 5 mm$^2$ for all four quadrants.

Figure 4:
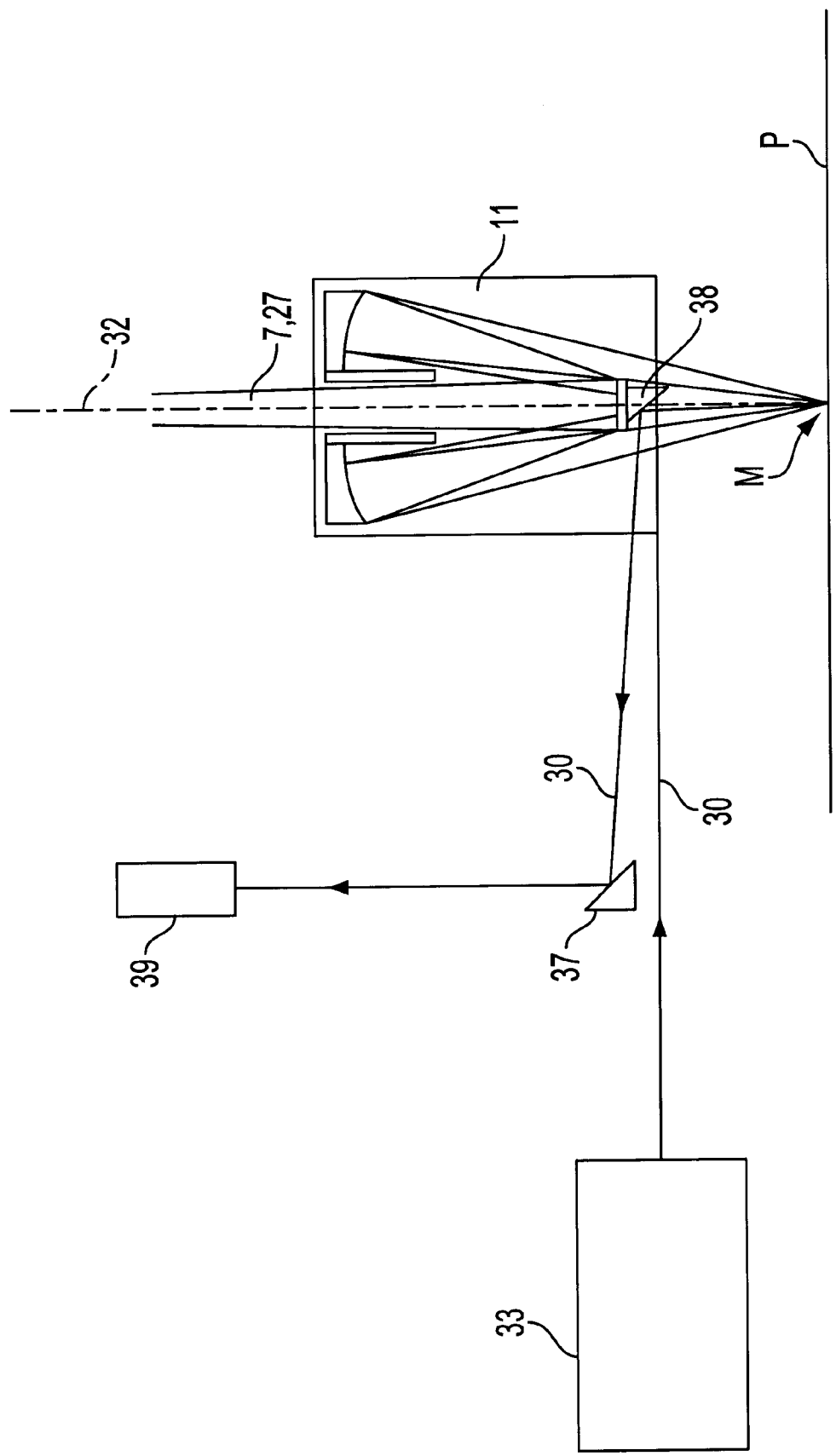
FIG. 4 shows a second variant of the manner in which the direction monitoring beam is guided according to the present invention.

The procedure for leveling the specimen will be explained later. Reference will first be made to a second variant of leveling device 29 that is depicted in FIG. 4. What is provided here once again, for example, is diode laser 33 with a wavelength $\lambda=670$ nm, the light of which, also focused by an optical system 34 (not depicted in FIG. 4), is directed as direction monitoring beam 30 onto the surface of specimen P. In contrast to the variant shown in FIG. 2, however, no polarization splitter and no $\lambda/4$ plate are provided in the beam path. It should be noted, however, that the orientation of direction monitoring beam 30 directed onto measurement location M does not correspond exactly to the direction of angle bisector 25, but rather that direction monitoring beam 30 is inclined at a small angle with respect to angle bisector 25.

The effect of this inclination is that direction monitoring beam 30 is not reflected from the specimen surface back in the same direction from which it was directed onto the specimen surface, with the result that it travels back not into diode laser 33 but onto a correspondingly positioned deflection prism 37, and is directed by the latter onto four-quadrant sensor 39. The advantageous result of this is that the number of optical assemblies is further reduced (since the polarization splitter and $\lambda/4$ plate are absent), and moreover that the incident and reflected paths of direction monitoring beam 30 are decoupled from one another.

Figure 5:
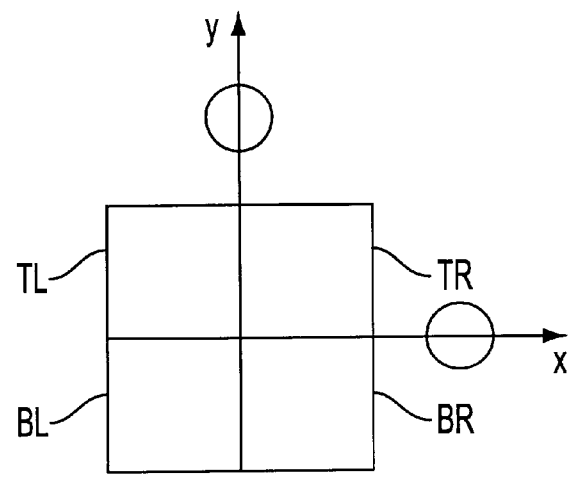
FIG. 5 shows a view toward the receiving surfaces of the four-quadrant receiver.

FIG. 5 depicts, by way of example, the four quadrants of four-quadrant sensor 39. Also drawn in are the X axis and Y axis to which the measurements are referred.

The quadrants are defined as TL, BL, TR, and BR. Four-quadrant sensor 39 is used as a zero detector, i.e. when the same quantity of light from the reflected direction monitoring beam 30 with a round cross section is falling on each of the four quadrants TL, BL, TR, and BR, the following mathematical relationships exist for the electrical voltages available at the output of the detector:

for the X axis $0=(U_{TR}+U_{TL})-(U_{BR}+U_{BL})$
for the Y axis $0=(U_{TL}+U_{BL})-(U_{TR}+U_{BR})$
for the reflectivity p $U_p=(U_{TL}+U_{BL}+U_{TR}+U_{BR})$ Four-quadrant sensor 39 is thus used to generate an angular difference signal X, an angular difference signal Y, and a summed signal (in terms of reflectivity). The summed signal can be used, by way of an interposed control section, to adapt the output of diode laser 33 to the reflectivity of the wafer surface. This can be done, for example by pulse modulation, by increasing the pulse width and thus the output of the diode laser as the reflectivity declines, and conversely decreasing them as the reflectivity rises.

The angular difference signals are converted, via an evaluation circuit 46 that is configured as a digital controller, into positioning commands for a positioning system 47, 47a that is connected to specimen stage 12.

Figure 6:
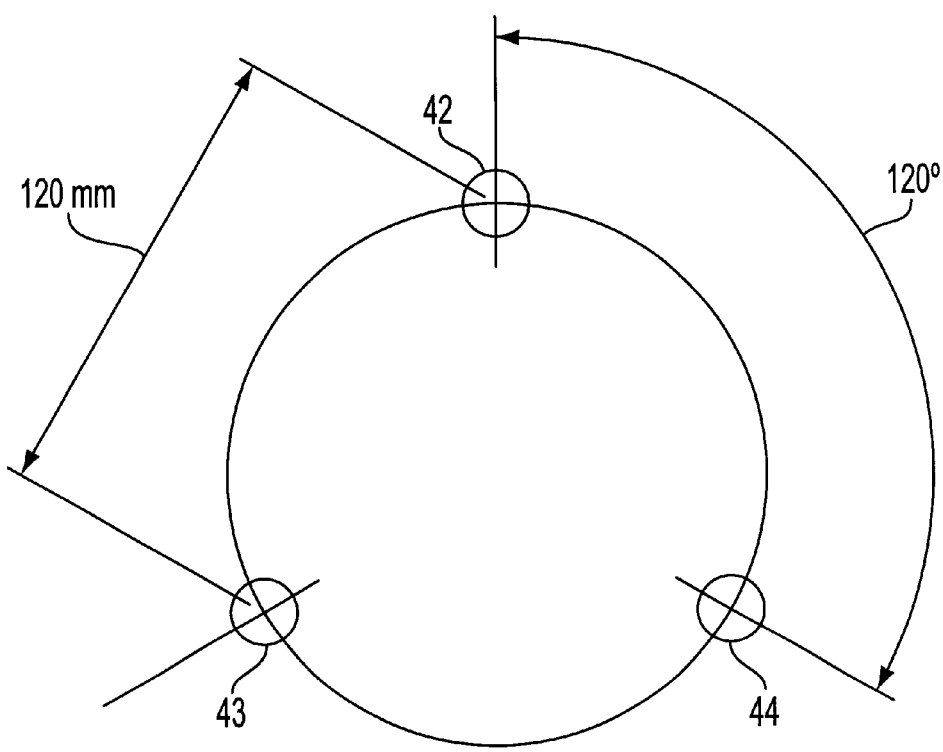
FIG. 6 shows the support positions of the specimen stage on the positioning system.

The configuration and operation of positioning system 47, 47a will first be explained with reference to FIG. 6, which depicts in plan view three support positions 42, 43, and 44 for specimen stage 12. The three support positions 42, 43, and 44 are arranged with radial symmetry on a circular circumference, i.e. they are equally far apart from one another on the circumference. The distance between each two support positions 42, 43, and 44, measured in a straight line, can advantageously be defined as 120 mm. Support at position 42 is implemented by way of a frame-mounted support bearing. Specimen stage 12 is supported in single-point fashion in each case, and can be tilted about support position 42.

The other two support positions 43 and 44 are each constituted by a piezo-translator. The piezo-translators, which are not depicted in the drawing, should preferably have a stroke length of approx. 200 $\mu$m; depending on the direction of the change in length, specimen stage 12 is raised or lowered at support position 43 or support position 44 or at both support positions 43 and 44, and thereby (since the height of support position 42 remains constant) tilted with respect to the plane of the drawing.

The tilting of specimen stage 12 also causes normal line N to tilt, and by controlled activation of the piezo-translators it is thus possible to achieve a defined change in the inclination of normal line N.

This tilting is performed by way of the positioning commands already referred to, which are dependent in the manner already described how the reflected direction monitoring beam 30 is imaged onto four-quadrant detector 39.

Figure 7:
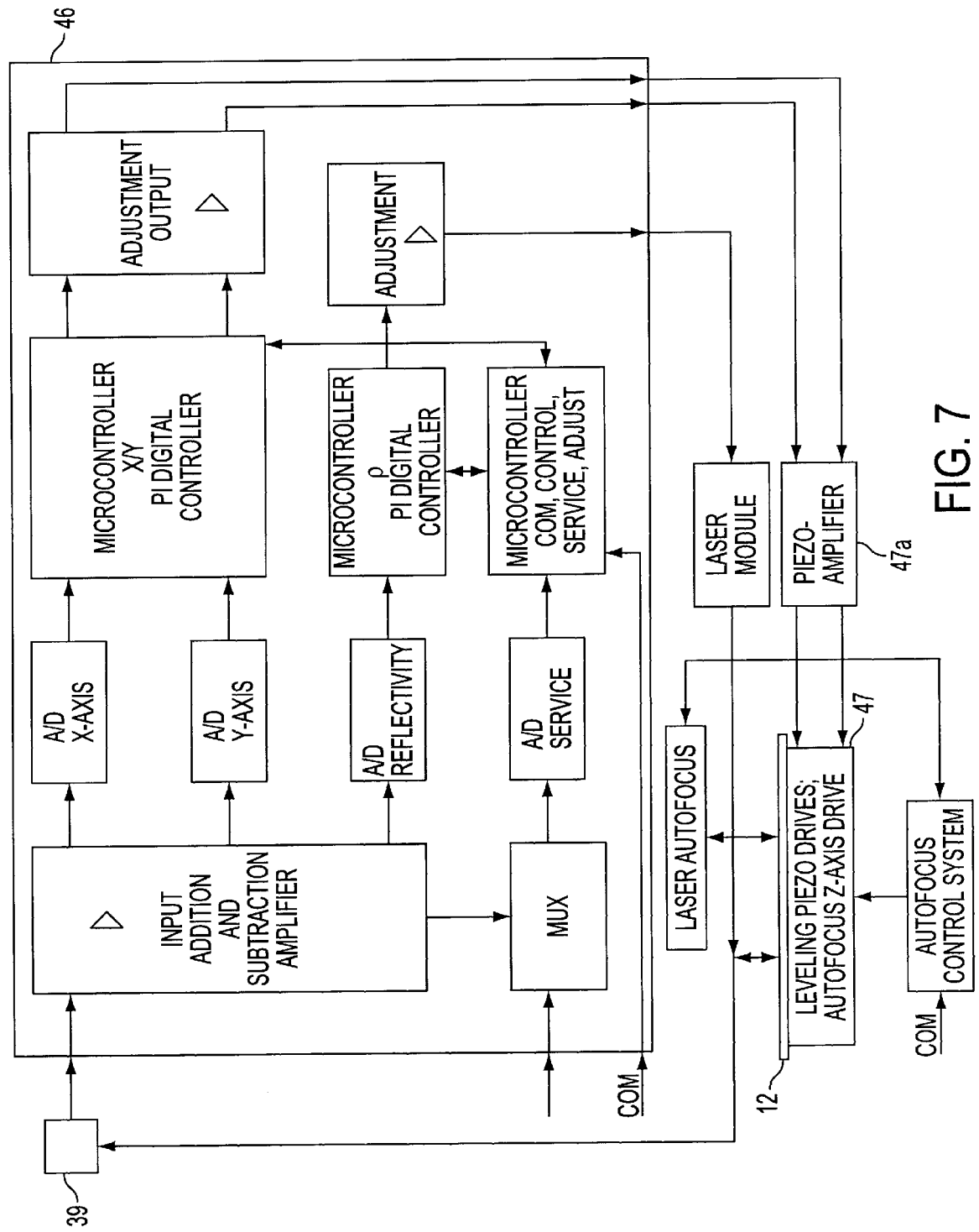
FIG. 7 shows a schematic depiction of the evaluation circuit that is part of the leveling device.

An example of the embodiment of evaluation circuit 46 to obtain positioning commands is depicted in FIG. 7. In this, an input addition and subtraction amplifier is provided to implement the mathematical relationships (described above) among quadrants TL, BL, TR, and BR, and the output of four-quadrant sensor 39 is delivered to its input. Individual microcontrollers provide communication, control, alignment, and service; pulse-width control in terms of reflectivity; and pulse-width control in terms of pivoting about the X and Y axes. Respective A/D converters are present between the input amplifier and the microcontrollers for signal matching. The outputs of the microcontrollers are connected via amplifiers to diode laser 33 (for readjustment of laser direction) and to the piezo-translators (to raise or lower support positions 43 and 44).

The result is to achieve, according to the present invention, a compact configuration for the device as a whole and furthermore to ensure that leveling and focusing are decoupled from one another during operation of the device. The following measurement sequence can thus advantageously be performed with this device:

- select the location on the surface of specimen P to be measured;
- find and capture the selected measurement location M using CCD camera 13;
- measure the orientation of normal line N using the leveling device;
- correct the deviation of normal line N using the leveling device;
- measure the focal position of the specimen surface in the target region;
- correct deviations in focal position by way of a separate autofocus control system that is also coupled to the specimen stage; and lastly
- measure the layer thickness either with the spectrophotometer or with ellipsometer 45, or with both measurement systems.

1 Illumination apparatus
2 Halogen lamp
3 Deuterium lamp
4 Lens
5 Illumination beam path
6 Beam splitter
7 Specimen measurement beam
8 Reference beam path
9 Spectrograph
10 Deflection mirrors
11 Mirror objective
12 Specimen stage
13 CCD camera
14 Beam path
15 Pinhole mirror
16 Line
17 Xenon lamp
18 Polarizer
19 Lens
20 Objective
21 Analyzer
22 Evaluation unit
23 Incident beam
24 Return beam
25 Angle bisector
26 Focus measurement system
27 Focus measurement beam
28 Mirror
29 Leveling device
30 Direction monitoring beam
32 Optical axis
33 Diode laser
34 Optical system
35 Polarization splitter
$\mp\lambda/4$ plate
37, 38 Deflection element (deflection mirror, deflection prism)
39 Four-quadrant sensor
40 Hollow beam cone
41 Central mirror
41a Shadow region
42, 43, 44 Support positions
45 Ellipsometer
46 Evaluation circuit
47, 47a Positioning system
M Measurement location
N Normal line
P Specimen

What is claimed is:

1. An optical measurement arrangement, comprising:

an ellipsometer (45) in which an incident beam (23) of polarized light is directed at an angle $\alpha\neq 90°$ onto a measurement location (M) on the surface of a specimen (P), and information as to specimen properties is obtained from an investigation of the reflected return beam (24);

a device for ascertaining and correcting directional deviations between a line normal to the specimen surface and an angle bisector (25) between the incident and return beams (23, 24);

an optical radiation source (33) emitting a direction monitoring beam (30) which is directed onto the measurement location (M) substantially in the direction of the angle bisector (25);

a position-sensitive area detector (39) and a reflective optical element for imaging a return reflection of the direction monitoring beam (30) onto the position-sensitive area detector (39);

an evaluation circuit (46) to which the position-sensitive area detector (39) is connected and said evaluation circuit (46) is for determining positions commands; and a positioning system (47, 47a) receiving the positioning commands of the evaluation circuit (46), wherein a specimen stage (12) on which the specimen (P) rests is caused to tilt until the position of the return reflection of the direction monitoring beam (30) on the position-sensitive area detector (39) corresponds to a predefined position at which the direction of the line normal to the specimen surface corresponds to the direction of the angle bisector (25), wherein the optical radiation source (33) is a focusable diode laser, and wherein a polarization splitter (35) and a $\lambda/4$ plate (36) following the polarization splitter (35) are present in the beam path between the diode laser (33) and the surface of the specimen (P), the return reflection of the direction monitoring beam (30) from the polarization splitter (35) being directed onto the position-sensitive area detector (39).

2. The optical measurement arrangement as defined in claim 1, wherein the position-sensitive area detector (39) is a four-quadrant detector.

3. The optical measurement arrangement as defined in claim 1, wherein the information as to specimen properties comprises layer thicknesses.

4. The optical measurement arrangement as defined in claim 1, wherein the positioning system (47, 47a) comprises at least two piezo-translators which are mounted to the specimen stage (12), wherein the specimen stage (12) rests on the piezo-translators in three support positions (42, 43, 44).

5. The optical measurement arrangement as defined in claim 4, wherein the piezo-translators having a stroke length of 200 $\mu$m.

6. The optical measurement arrangement as defined in claim 1, further comprising a spectrophotometer and a mirror objective (11) for illuminating the measurement location (M) and for receiving light reflected from the measurement location (M) and directing the reflected light to a spectrograph (9) of the spectrometer, wherein the mirror objective (11) defines an unused aperture space and the optical element (38) is provided in said unused aperture space for directing the direction monitoring beam (30) to and from the measurement location (M).

7. The optical measurement arrangement as defined in claim 6, wherein the optical element (38) comprises a deflection mirror and the specimen measurement beam (7)

comprises a hollow beam cone (40), proceeding from the mirror objective (11), whose conical tip lies in the measurement location (M), and the direction monitoring beam (30) extends inside the hollow beam cone (40).

8. The optical measurement arrangement as defined in claim 7, wherein the deflection mirror (38) is embodied with a truncated conical outer contour and is attached to the mirror objective (11).

9. The optical measurement arrangement as defined in claim 1, wherein a focus measurement system (26) is provided, in which a focus measurement beam (27) proceeding from a laser diode is directed onto the measurement location (M) of the specimen (P).

10. A measurement arrangement comprising:
   a mirror arrangement (11) having a central mirror (41) that defines a shadow region (41a) and an optical axis (32), the mirror arrangement (11) illuminating and imaging a measurement location (M) on a specimen (P),
   a leveling device (29) having an optical radiation source (33), a direction monitoring beam (30), and a spatially resolving detector (39) and
   at least one optical element (38) being arranged in the shadow region (41a) of the central mirror (41) of the mirror arrangement (11), wherein said at least one optical element (38) guides the direction monitoring beam (30) substantially along the optical axis (32) of the mirror arrangement (11) and directs it onto the measurement location (M) of the specimen (P), and wherein said at least one optical element (38) directs the direction monitoring beam (30) reflected from the measurement location (M) onto the spatially resolving detector (39).

11. The measurement arrangement as defined in claim 10, wherein the optical element (38) is arranged such that the direction monitoring beam (30) is aligned parallel to the optical axis (32) of the mirror arrangement (11); and that a beam splitter (35) is provided to couple out the direction monitoring beam (30) reflected from the measurement location (M) and direct it onto the spatially resolving detector (39).

12. The measurement arrangement as defined in claim 10, wherein the optical element (38) is arranged such that the direction monitoring beam (30) directed onto the measurement location (M) and reflected from the measurement location (M) is slightly inclined with respect to the optical axis (32) of the mirror arrangement (11).

13. The measurement arrangement as defined in claim 10, wherein a deflection element (37) is provided between the optical element (38) and the spatially resolving detector (39) to direct the direction monitoring beam (30) reflected from the measurement location (M) onto the detector (39).

14. The measurement arrangement as defined in claim 10, wherein the signals supplied by the spatially resolving detector (39) correspond to the inclinational deviation of a line perpendicular to the measurement location (M) from the optical axis (32).

15. The measurement arrangement as defined in claim 10, wherein an evaluation circuit (46) for evaluating the detector signals of the spatially resolving detector (39) and a positioning system (47, 47a) for modifying the inclination of the specimen (P) are provided for regulating the inclinational deviation of a line perpendicular to the measurement location (M) from the optical axis (32) to a specific value.

16. The measurement arrangement as defined in claim 10, wherein the spatially resolving detector (39) is a four-quadrant detector.

17. The measurement arrangement as defined in claim 10, wherein an optical radiation (7, 27) passing through the mirror arrangement (11 emanates from an illumination apparatus (1) and is directable to one of an electronic imaging device (13) and a spectrograph (9).

18. The measurement arrangement as defined in claim 10, wherein an ellipsometer (45) is provided for ellipsometric measurement of the measurement location (M).

19. A method for measuring an inclination between a line perpendicular to a measurement location (M) on a specimen (P) and an optical axis defined by an objective (11) for imaging the measurement location (M), comprising:
   generating a direction monitoring beam (30) by a radiation source (33);
   delivering the direction monitoring beam (30) to the optical axis (32) of the objective (11), wherein the direction monitoring beam (30) arrives in a region between the objective (11) and the measurement location (M);
   deflecting the direction monitoring beam (30) toward the measurement location (M);
   reflecting the direction monitoring beam (30) at the measurement location (M);
   deflecting the reflected direction monitoring beam (30) out of the vicinity of the optical axis (32), specifically in a region between the objective (11) and the measurement location (M);
   receiving the deflected direction monitoring beam (30) by a spatially resolving detector (39); and
   determining from the signals of the detector (39) the inclination between the line perpendicular to the measurement location (M) and the optical axis (32) of the objective (11).

20. The method as defined in claim 19, wherein the direction monitoring beam (30) is parallel to the optical axis (32) of the objective (11) in the region between the objective (11) and the measurement location (M).

21. The method as defined in claim 19, wherein the direction monitoring beam (30) has a slight inclination relative to the optical axis (32) of the objective (11) in the region between the objective (11) and the measurement location (M).

22. The method as defined in claim 19, wherein the objective (11) is a mirror objective having a central mirror (41) and the central mirror (41) defines a shadow region (41a), and deflecting the direction monitoring beam (30) is accomplished in the shadow region (41a) of the central mirror (41) of the mirror objective.

23. The method as defined in claim 19, comprising:
   evaluating the signals of the detector (39) with an evaluation circuit (46); and
   adjusting the inclination of the specimen (P) with of a positioning system (47, 47a) such that a predefined angle between the line perpendicular to the measurement location (M) of the specimen (P) and the optical axis (32) of the objective (11) is established.

24. The method as defined in claim 19, comprising:
   evaluating the signals of the detector (39) with an evaluation circuit (46); and
   adjusting the inclination of the specimen (P) with a positioning system (47, 47a) such that the optical axis (32) of the objective (11) is perpendicular to the measurement location (M).

* * * * *